United States Patent [19]

Edwards et al.

[11] Patent Number: 5,428,019
[45] Date of Patent: Jun. 27, 1995

[54] BOMBESIN ANALOGS

[75] Inventors: Judson V. Edwards; Bradford O. Fanger, both of Cincinnati, Ohio

[73] Assignee: Merrell Dow Pharmaceuticals Inc., Cincinnati, Ohio

[21] Appl. No.: 213,378

[22] Filed: Mar. 14, 1994

Related U.S. Application Data

[63] Continuation of Ser. No. 88,413, Jul. 16, 1993, abandoned, which is a continuation of Ser. No. 704,863, May 23, 1991, abandoned.

[51] Int. Cl.$^6$ .......... A61K 38/00; C07K 5/00; C07K 7/00; C07K 17/00
[52] U.S. Cl. .......... 514/16; 514/15; 530/327; 530/328
[58] Field of Search .......... 530/327, 328; 514/14, 514/15, 16

[56] References Cited

U.S. PATENT DOCUMENTS

| | | | |
|---|---|---|---|
| 4,297,346 | 10/1981 | Rips et al. | |
| 4,421,744 | 12/1983 | Gormley | |
| 4,631,270 | 12/1986 | Yankeelov et al. | 514/15 |
| 4,871,717 | 10/1989 | Coy et al. | 514/11 |
| 5,028,692 | 7/1991 | Oliff et al. | |
| 5,047,502 | 9/1991 | Oliff et al. | |

FOREIGN PATENT DOCUMENTS

| | | |
|---|---|---|
| 309297 | 9/1988 | European Pat. Off. |
| 313158 | 10/1988 | European Pat. Off. |
| 315367 | 10/1988 | European Pat. Off. |
| 339193 | 2/1989 | European Pat. Off. |
| 345990 | 5/1989 | European Pat. Off. |
| 434979 | 11/1990 | European Pat. Off. |
| 8909232 | 10/1989 | WIPO |
| 9001037 | 2/1990 | WIPO |
| 9003980 | 4/1990 | WIPO |
| 9106563 | 5/1991 | WIPO |

OTHER PUBLICATIONS

Coy et al., J. Biol Chem., vol. 263, No. 11, pp. 5056–5060, 1989.
Coy et al., J. Biol Chem., vol. 264, No. 25, pp. 14691–14697, 1989.
E. A. Van Tol et al., Intravenous Administration of Bombesin in Man Stimulates Natural Killer Cell Activity AGaint Tumour Cells, Neuropeptides 18, pp. 15–21, 1991.
Heimbrook, David C., et al., J. Biol. Chem. 264(19), 11258–11262 (1989).
Mukai, Hidehito, et al., Am. Physiol. Soc., E235 (1989).
Heimbrook, David D., UCLA Symp., Mol. Cel. Biolo., 86, 295–307 (1989).
Saeed, Z. A., Peptides, 10, 597–603 (1989).
Woll, Pennela, J. et al., Proc. Natl. Acad. Sci. USA, 85, 1859–1863 (1988).
Zhang, Li, et al., BBA 972, 37–44 (1988).
Woll, Pennela, J. et al., Growth Factors, 1, 75–83 (1988).
Bepler, Gerold, et al., Peptides, 9, 1367–1372 (1989).
Merali, Zul, et al., Synapse, 2, 282–287 (1988).
Dutta, Anand S., et al., J. Med. Chem. 29, 1171–78 (1986).
Marki, et al., Peptides, 2(2) 169–177 (1981).
Lebacq-Verheyden, A. M., et al., Bombesin and Gastrin Releasing Peptide Neuropeptides, Secretogogues, and Growth Factors, Chapter 21, In Peptide Growth Factors and Their Receptors II, editors Sporn, M., and Roberts, A. B., Springer-Verlag, NY (1990).

(List continued on next page.)

Primary Examiner—Jill Warden
Assistant Examiner—A. M. Davenport
Attorney, Agent, or Firm—Kenneth J. Collier

[57] ABSTRACT

Agonists and Antagonist of bombesin are derivatives of naturally occurring bombesin possessing a methyl sulfide or a methyl amide bond connecting the two amino acids on the carboxy terminal end. Agonist and antagonist activities are confirmed using conventional competitive binding and biochemical assays as well as conventional physiological tests and the use of these derivatives in a variety of conditions. Use of these peptides include stimulating or antagonizing growth of tissues, especially lung, and a means for effecting treatment for digestional disorders. Treatment comprises administering to a patient in need thereof, an effective amount of a bombesin analog.

9 Claims, 3 Drawing Sheets

OTHER PUBLICATIONS

Erspamer, G. F., et al, Regulatory Peptides, 21, 1–11 (1988).
Edwards, J. V., et al, 1990 Gordon Conference on the Chemistry and Biology of Peptides, Feb. 5–9, 1990 Ventura, Calif.
Antony, V. B., et al., Clin. Res. 37, 145A (1989).
Woll, P. J., et al., BBRC, 155(1), Aug., 359–365 (1988).
Spatola, A. F., et al., Chem. Abs. 111(11), abst. No. 90576e (1989).
Smith, C. W., et al., Chem Abs. 109(3), abst. No. 23372f, 662 (1988).
Edwards, J. V., et al., BBRC 136(2), 730–6 (1986).
Edwards, J. V., et al., Int. J. Peptide Protein Res. 28, 603–612 (1986).
Edwards, J. V., et al., 1992 Gordon Conference–Peptides, Chemistry and Biology, Ventura, Calif., Feb. 9–14, 1992.
Mahmoud, S., et al., Life Sciences, 44(5), 367–373 (1989).
Rossowski, W. J., et al., Scand. J. Gastroenterol., 24(1), 121–128 (1989).
Bologona, Mauro, et al., Cancer, 63, 1714–1720 (1989).
Jensen, R. T., et al., Nature, 309, 61–63 (1984).
Cowan, Alan, TIPPS, 101, 1–3 (1988).
Edwards, et al., "Potent pseudopeptide bombesin–like agonists and antagonists", Int. J. Peptide Protein Res., 43, 374–383 (1994).
Edwards, et al., "Potent bombesin–like agonists and antagonists: structure/activity at the COOH— and $NH_2$—termini", 13th American Peptide Symposium, Robert S. Hughes & John A. Smith, eds., pp. 505–507, ESCOM–Leiden (1994).

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1..14
      ( D ) OTHER INFORMATION: /note="Gastrin Releasing Peptide amino acids 14-27"

( i x ) FEATURE:
      ( A ) NAME/KEY: Modified-site
      ( B ) LOCATION: 14
      ( D ) OTHER INFORMATION: /note="Xaa is Methionin-1-amide (Met-NH2)"

( x i ) SEQUENCE DESCRIPTION: SEQ ID NO:1:

Met Tyr Pro Arg Gly Asn His Trp Ala Val Gly His Leu Xaa
1               5                   10

( 2 ) INFORMATION FOR SEQ ID NO:2:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note="Xaa is pyroglutamyl (pGlu)"

( i x ) FEATURE:
      ( A ) NAME/KEY: Modified-site
      ( B ) LOCATION: 14
      ( D ) OTHER INFORMATION: /note="Xaa is Methionin-1-amide (Met-NH2)"

( x i ) SEQUENCE DESCRIPTION: SEQ ID NO:2:

Xaa Gln Arg Leu Gly Asn Gln Trp Ala Val Gly His Leu Xaa
1               5                   10

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( D ) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is pyroglutamyl (pGlu)"

(ix) FEATURE:
    (A) NAME/KEY: Modified-site
    (B) LOCATION: 9
    (D) OTHER INFORMATION: /note="Xaa is Methionin-1-amide (Met-NH2)"

(xi) SEQUENCE DESCRIPTION: SEQ ID NO:3:

Xaa Gln Trp Ala Val Gly His Phe Xaa
1                 5

(2) INFORMATION FOR SEQ ID NO:4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is pyroglutamyl (pGlu)"

(ix) FEATURE:
    (A) NAME/KEY: Modified-site
    (B) LOCATION: 13
    (D) OTHER INFORMATION: /note="Xaa is a Leucine analog
        having a 1- methylene group, in place of a
        1-carbonyl group, bonded to the alpha"

(ix) FEATURE:
    (A) NAME/KEY: Modified-site
    (B) LOCATION: 13
    (D) OTHER INFORMATION: /note="(cont'd) nitrogen of the
        subsequent amino acid"

(ix) FEATURE:
    (A) NAME/KEY: Modified-site
    (B) LOCATION: 14
    (D) OTHER INFORMATION: /note="Xaa is Leucin-1-amide (Leu-NH2)"

(xi) SEQUENCE DESCRIPTION: SEQ ID NO:4:

Xaa Gln Arg Leu Gly Asn Gln Trp Ala Val Gly His Xaa Xaa
1                 5                           10

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is pyroglutamyl (pGlu)"

(ix) FEATURE:
    (A) NAME/KEY: Modified-site
    (B) LOCATION: 13
    (D) OTHER INFORMATION: /note="Xaa is a Phenylalanine
        analog having a 1-methylene group, in place of a
        1-carbonyl group, bonded to the alpha"

(ix) FEATURE:
    (A) NAME/KEY: Modified-site
    (B) LOCATION: 13

(D) OTHER INFORMATION: /note="(cont'd) nitrogen of the
   subsequent amino acid"

(ix) FEATURE:
   (A) NAME/KEY: Modified-site
   (B) LOCATION: 14
   (D) OTHER INFORMATION: /note="Xaa is
       2-thio-4- methylpent-1-amide ([S]Leu-NH2)"

(xi) SEQUENCE DESCRIPTION: SEQ ID NO:5:

Xaa Gln Arg Leu Gly Asn Gln Trp Ala Val Gly His Xaa Xaa
1               5                   10

(2) INFORMATION FOR SEQ ID NO:6:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note="Xaa is pyroglutamyl (pGlu)"

(ix) FEATURE:
       (A) NAME/KEY: Modified-site
       (B) LOCATION: 8
       (D) OTHER INFORMATION: /note="Xaa is a Phenylalanine
           analog having a 1-methylene group, in place of a
           1-carbonyl group, bonded to "

(ix) FEATURE:
       (A) NAME/KEY: Modified-site
       (B) LOCATION: 8
       (D) OTHER INFORMATION: /note="(cont'd) the alpha nitrogen
           of the subsequent amino acid"

(ix) FEATURE:
       (A) NAME/KEY: Modified-site
       (B) LOCATION: 9
       (D) OTHER INFORMATION: /note="Xaa is
           2-thio-4- methylpent-1-amide ([S]Leu-NH2)"

(xi) SEQUENCE DESCRIPTION: SEQ ID NO:6:

Xaa Gln Trp Ala Val Gly His Xaa Xaa
1               5

(2) INFORMATION FOR SEQ ID NO:7:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note="Xaa is pyroglutamyl (pGlu)"

(ix) FEATURE:
       (A) NAME/KEY: Modified-site
       (B) LOCATION: 8
       (D) OTHER INFORMATION: /note="Xaa is a Phenylalanine
           analog having a 1-methylene group, in place of a
           1-carbonyl group, bonded to the alpha"

(ix) FEATURE:
       (A) NAME/KEY: Modified-site
       (B) LOCATION: 8
       (D) OTHER INFORMATION: /note="(cont'd) nitrogen of the
           subsequent amino acid"

(ix) FEATURE:

(A) NAME/KEY: Modified-site
                (B) LOCATION: 9
                (D) OTHER INFORMATION: /note="Xaa is
                    2-sulfoxide- 4-methylpent-1-amide ([S]Leu-NH2)"

(xi) SEQUENCE DESCRIPTION: SEQ ID NO:7:

Xaa Gln Trp Ala Val Gly His Xaa Xaa
     1               5

(2) INFORMATION FOR SEQ ID NO:8:

(i) SEQUENCE CHARACTERISTICS:
                (A) LENGTH: 9 amino acids
                (B) TYPE: amino acid
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note="Xaa is pyroglutamyl (pGlu)"

(ix) FEATURE:
                (A) NAME/KEY: Modified-site
                (B) LOCATION: 8
                (D) OTHER INFORMATION: /note="Xaa is a Phenylalanine
                    analog having a 1-methylene group, in place of a
                    1-carbonyl group, bonded to the alpha"

(ix) FEATURE:
                (A) NAME/KEY: Modified-site
                (B) LOCATION: 8
                (D) OTHER INFORMATION: /note="(cont'd) nitrogen of the
                    subsequent amino acid"

(ix) FEATURE:
                (A) NAME/KEY: Modified-site
                (B) LOCATION: 9
                (D) OTHER INFORMATION: /note="Xaa is
                    N-methyl- leucin-1-amide"

(xi) SEQUENCE DESCRIPTION: SEQ ID NO:8:

Xaa Gln Trp Ala Val Gly His Xaa Xaa
     1               5

(2) INFORMATION FOR SEQ ID NO:9:

(i) SEQUENCE CHARACTERISTICS:
                (A) LENGTH: 9 amino acids
                (B) TYPE: amino acid
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note="Xaa is pyroglutamyl (pGlu)"

(ix) FEATURE:
                (A) NAME/KEY: Modified-site
                (B) LOCATION: 8
                (D) OTHER INFORMATION: /note="Xaa is Phenylalanine analog
                    having a 1- methylene group, in place of a
                    1-carbonyl group, bonded to the"

(ix) FEATURE:
                (A) NAME/KEY: Modified-site
                (B) LOCATION: 8
                (D) OTHER INFORMATION: /note="(cont'd) alpha nitrogen of
                    the subsequent amino acid"

(ix) FEATURE:
                (A) NAME/KEY: Modified-site
                (B) LOCATION: 9
                (D) OTHER INFORMATION: /note="Xaa is
                    2-thiomethyl- 4-methylpent-1-amide ([

S(CH3)]Leu- NH2)"

( x i ) SEQUENCE DESCRIPTION: SEQ ID NO:9:

Xaa Gln Trp Ala Val Gly His Xaa Xaa
1               5

( 2 ) INFORMATION FOR SEQ ID NO:10:

( i ) SEQUENCE CHARACTERISTICS:
     ( A ) LENGTH: 7 amino acids
     ( B ) TYPE: amino acid
     ( D ) TOPOLOGY: linear ( i i ) MOLECULE TYPE: peptide ( i x ) FEATURE:
     ( A ) NAME/KEY: Modified-site
     ( B ) LOCATION: 1
     ( D ) OTHER INFORMATION: /note="Xaa is
         N-alpha- acetyl-glutamine (Ac-Gln)"

( i x ) FEATURE:
     ( A ) NAME/KEY: Modified-site
     ( B ) LOCATION: 5
     ( D ) OTHER INFORMATION: /note="Xaa is D-alanine (D-Ala or
         ala)"

( i x ) FEATURE:
     ( A ) NAME/KEY: Modified-site
     ( B ) LOCATION: 7
     ( D ) OTHER INFORMATION: /note="Xaa is Leucin-1-amide
         ( L e u - N H 2 )"

( x i ) SEQUENCE DESCRIPTION: SEQ ID NO:10:

Xaa Trp Ala Val Xaa His Xaa
1           5

( 2 ) INFORMATION FOR SEQ ID NO:11:

( i ) SEQUENCE CHARACTERISTICS:
     ( A ) LENGTH: 7 amino acids
     ( B ) TYPE: amino acid
     ( D ) TOPOLOGY: linear ( i i ) MOLECULE TYPE: peptide ( i x ) FEATURE:
     ( A ) NAME/KEY: Modified-site
     ( B ) LOCATION: 1
     ( D ) OTHER INFORMATION: /note="Xaa is
         N-alpha- octanoyl-glutamine (Oct-Gln)"

( i x ) FEATURE:
     ( A ) NAME/KEY: Modified-site
     ( B ) LOCATION: 5
     ( D ) OTHER INFORMATION: /note="Xaa is D-alanine (D-Ala or
         ala)"

( i x ) FEATURE:
     ( A ) NAME/KEY: Modified-site
     ( B ) LOCATION: 7
     ( D ) OTHER INFORMATION: /note="Xaa is Leucin-1-amide
         ( L e u - N H 2 )"

( x i ) SEQUENCE DESCRIPTION: SEQ ID NO:11:

Xaa Trp Ala Val Xaa His Xaa
1           5

( 2 ) INFORMATION FOR SEQ ID NO:12:

( i ) SEQUENCE CHARACTERISTICS:
     ( A ) LENGTH: 7 amino acids
     ( B ) TYPE: amino acid
     ( D ) TOPOLOGY: linear ( i i ) MOLECULE TYPE: peptide (ix) FEATURE:
    (A) NAME/KEY: Modified-site
    (B) LOCATION: 1
    (D) OTHER INFORMATION: /note="Xaa is
        N-alpha- lauryl-glutamine"

(ix) FEATURE:
    (A) NAME/KEY: Modified-site
    (B) LOCATION: 5
    (D) OTHER INFORMATION: /note="Xaa is D-alanine (D-Ala or
        ala)"

(ix) FEATURE:
    (A) NAME/KEY: Modified-site
    (B) LOCATION: 7
    (D) OTHER INFORMATION: /note="Xaa is Leucin-1-amide
        (Leu-NH2)"

(xi) SEQUENCE DESCRIPTION: SEQ ID NO:12:

Xaa Trp Ala Val Xaa His Xaa
1               5

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is
            N-alpha- palmityl-glutamine"

(ix) FEATURE:
        (A) NAME/KEY: Modified-site
        (B) LOCATION: 5
        (D) OTHER INFORMATION: /note="Xaa is D-alanine (D-Ala or
            ala)"

(ix) FEATURE:
        (A) NAME/KEY: Modified-site
        (B) LOCATION: 7
        (D) OTHER INFORMATION: /note="Xaa is Leucin-1-amide
            (Leu-NH2)"

(xi) SEQUENCE DESCRIPTION: SEQ ID NO:13:

Xaa Trp Ala Val Xaa His Xaa
1               5

BOMBESIN ANALOGS

CROSS-REFERENCE TO RELATED APPLICATION

This is a continuation of application Ser. No. 08/088,413, filed Jul. 6, 1993, and now abandoned, which is a continuation of application Ser. No. 07/704,863 filed May 23, 1991, now abandoned.

FIELD OF INVENTION

This invention relates to novel Bombesin analogs to which are potentially useful as pharmaceuticals.

BACKGROUND OF INVENTION

Bombesin (ID#2) is a 14 amino acid peptide, originally isolated from the skin of the frog *Bombina bombina*. Bombesin is also structurally related to a number of other peptides including Gastrin Releasing Peptide (ID#1), and Litorin (ID#3) (See Sequence identification Section).

Bombesin is known to have a range of effects including stimulation of the nervous system, reduction of renal blood flow, secretion of pituitary hormones, growth promotion, memory retention, induction of myoelectric and contractile activity of intestinal myocytes, induction of gastric and pancreatic secretion, and bolstering of immune function. There has been considerable interest modulating these activities in the design and development of bombesin analogs as possible mimics or inhibitors of bombesin action in the body.

The bombesin-dependent responses occur through a class of high-affinity ($KD=1$ nm) cell surface receptors that bind bombesin. Binding of Bombesin to its cell surface receptor elicts cell mitogenic responses in a number of tissues. The mitogenic response has been demonstrated in a number of cell types including Swiss 3T3 embryo fibroblast cells, human bronchial epithelial cells, human small cell lung carcinoma cells, rat gastrin cells, and rat pancratic cells. Similarly, Bombesin induction of gastric and pancreatic secretions, important for digestive functions, occur through the receptors found on cells of pancreatic (B-Cells) and intestinal gastrin cells (G-cells).

Binding of Bombesin to its extracellular receptor evokes a number of intracellular signals including activation of G-proteins, which in turn activates phospholipase C (PLC). PLC in turn converts phosphatidylinositol phosphate (PI) into inositol 1,4,5,-triphosphate ($IP_3$) and diacylglycerol (DAG). $IP_3$ and DAG are believed to be intracellular signals for cellular mediated events.

Structure-activity studies indicate that receptor-binding requires a peptide ligand containing an amidated C-terminal, and generally the presence of the last eight amino acids. Recent work has concentrated on modifying the carboxy terminal (C-terminal) region of Bombesin to selectively modulated the receptor interaction utilizing a variety of different types of C-terminal modified analogs. These modifications have included, for example, incorporation of D-amino acids, non-peptide bonds, amide, and ester modifications. These alterations have given rise to certain peptides having improved characteristics.

The applicants have prepared linear peptide analogs of the natural bombesin containing a non-peptide bond between amino acids 8 and 9, consisting of a methyl sulfide group ($\Psi[CH_2S(CH_3)]$) or a methyl amide group ($\Psi[CH_2N(CH_3)]$). The applicants have demonstrated that these analogs act at the bombesin receptor and elicit or prevent required intracellular signals for cellular response of bombesin. The peptide analogs of this invention potentially possess significant mitotic and/or secretory activity and therefore may allow for a scientifically interesting and therapeutically significant adjunct to growth therapy and/or the treatment of digestive disorders. Moreover, the presence of methyl sulfide and methyl amide functionalities, or des-methionine analogs having D-amino acids and N-terminal modifications may provide for enhanced potency and extended duration of action.

SUMMARY OF TEE INVENTION

Claimed are peptide derivatives of the formula 1 given below:

$$X\text{-}A_1\text{-}A_2\text{-}A_3\text{-}A_4\text{-}A_5\text{-}A_6\text{-}A_7\text{-}A_8\text{-}\Psi\text{-}A_9\text{-}Y$$

wherein
- X is an amino terminal residue selected from hydrogen, one or two alkyl groups from 1 to 16 carbon atoms, one or two acyl groups of from 2 to 16 carbon atoms, carbobenzyloxy or t-butyloxy carbonyl; unless the amino terminal amino acid is a cyclic derivative and thereby X is omitted.
- $A_1$ is pGlu, Glu, or suitable acidic hydrophilic amino acid residue or is a sequence of 1 to 5 amino acids of Bombesin or a natural variants thereof, or a bond;
- $A_2$ is Gln, or suitable neutral amino acid residue;
- $A_3$ is Trp, or a suitable neutral or hydrophobic amino acid residue;
- $A_4$ is Ala, or a suitable neutral or hydrophobic amino acid residue;
- $A_5$ is Val, or a suitable neutral or hydrophobic amino acid residue;
- $A_6$ is Gly, Ala, ala, or a suitable neutral or hydrophobic amino acid residue;
- $A_7$ is His, a suitable neutral or basic hydrophilic amino acid residue;
- $A_8$ is Phe, Leu, or is a suitable hydrophobic amino acid residue;
- $\Psi$ is a dipeptide determinant of $A_8\Psi A_9$ wherein $\Psi$ is $[CH_2S(CH_3)]$ or $[CH_2N(CH_3)]$, and wherein and $A_8$ and $A_9$ designates the substituent amino acids;
- $A_9$ is Leu, Met, Nle or is a suitable hydrophobic amino acid residue or is a sequence of 1 to 5 amino acid residues of Bombesin or variants thereof, or a bond; and
- Y is a carboxy terminal substituent of the carbonyl group of the $A_9$ amino acid selected from OH, ($C_1$-$C_8$) alkoxyester, carboxamide, mono or di ($C_1$-$C_8$) alkyl amide, ($C_1$-$C_8$) alkylamine, ($C_1$-$C_4$) thioalkylether, or pharmaceutically acceptable salt thereof.

DETAILED DESCRIPTION OF THE INVENTION

Figure 1:
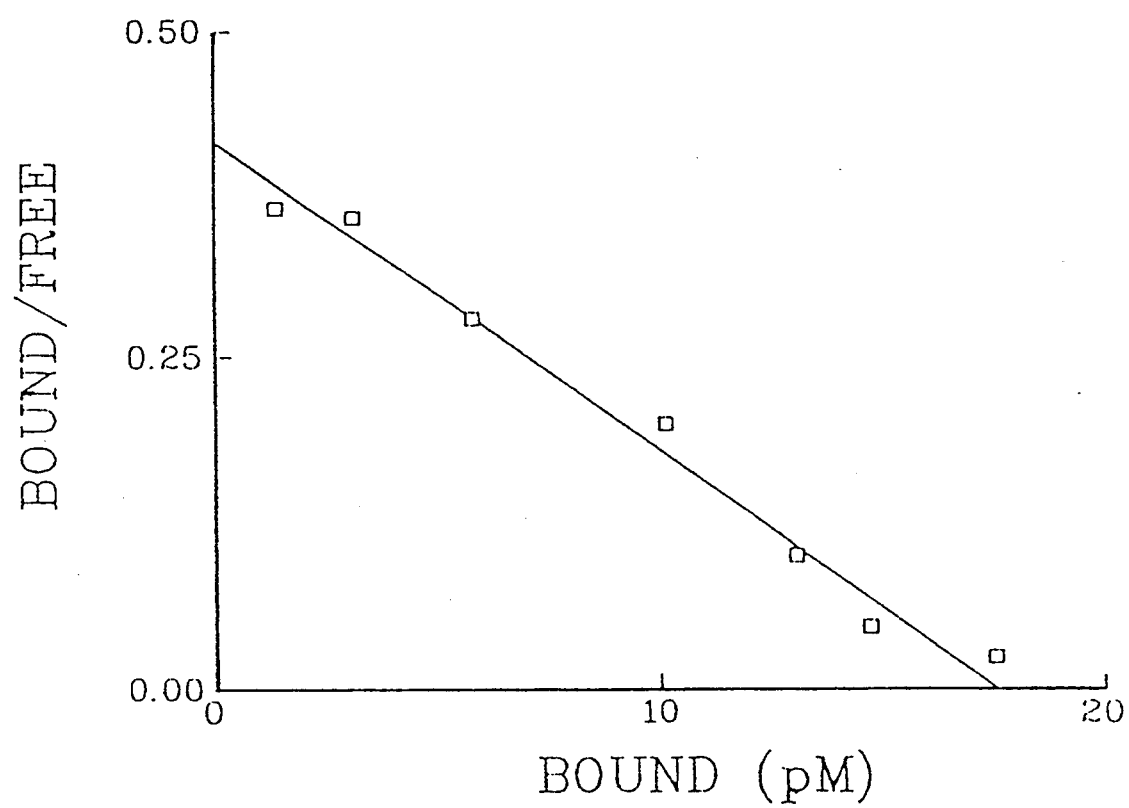
FIG. 1 illustrates that $^{135}$I-GRP binds to a single class of sites—the bombesn/GRP receptor—on murine pancreatic membranes (Example 1).

The following common abbreviations of; (1) amino acids and their three letter codes, and (2) terminal amino and carboxy substituents used throughout this specification:

| (1): THE AMINO ACIDS AND THEIR THREE LETTER CODE | |
|---|---|
| L-AMINO ACIDS | D-AMINO ACIDS |
| Ala - alanine | ala - D-alanine |
| Arg - arginine | arg - D-arginine |
| Asn - asparagine | asn - D-asparagine acid |
| Cys - cysteine | cys - D-cysteine |
| Gly - glycine | |
| Glu - glutamic acid | glu - D-glutamic acid |
| Val - valine | val - D-valine |
| Gln - glutamine | gln - D-glutamine |
| His - histidine | his - D-histidine |
| Ile - isoleucine | ile - D-isoleucine |
| Leu - leucine | leu - D-leucine |
| Lys - lysine | lys - D-lysine |
| Phe - phenylalanine | phe - D-phenylalanine |
| Met - methionine | met - D-methionine |
| Pro - proline | pro - D-proline |
| Ser - serine | ser - D-serine |
| Thr - threonine | thr - D-threonine |
| Trp - tryptophan | trp - D-tryptophan |
| Tyr - tyrosine | tyr - D-tyrosine |
| Nle - norleucine | |

| (2): AMINO AND CARBOXY TERMINAL ACID SUSTITUENTS |
|---|
| Ac - acetyl |
| Azt - azetidine-2-carboxylate |
| Cin - cinnamoyl |
| DhCin - 3,4-dihydrocinnamoyl |
| Glt - glutaryl |
| Mal - maleyl |
| Oac - 8-aminooctanoic acid |
| Oct - n-octane |
| Suc - succinyl |
| Glt - glutaryl |
| Tfa - trifloroacetyl |
| # - C-terminal amide |

As many as 13 bombesin-like peptides have been isolated from amphibian sources, one from arian proventriculus, and 5 or 6 from mammalian tissues. The Bombesin peptides may be divided into 3 subfamilies, on the basis of their primary structure, their pharmacological activity, and their receptor affinity. The bombesin subfamily is characterized by the C-terminal tetrapeptide —Gly—His—Leu—Met—$NH_2$, the litorin/ranatensin subfamily by the tetrapeptide —Gly—His—Phe—Met—$NH_2$, and the phyllolitorin subfamily by the tetrapeptide —Gly—Ser—Phe(Leu)—Met—$NH_2$.

Present within the bombesin subfamily are the gastrin-releasing peptides (GRPs) of mammalian origin. Human, porcine, and canine GRPs differ from each other in the N-terminal dodecapeptide, but have an identical carboxy amino acid sequences (residues 13–27). Moreover, the C-terminal decapeptide of the mammalian GRPs are identical to the C-terminal decapeptide of frog bombesin, with only the difference of having a His residue substituted for the Gln residue at position 8 from the C-terminus. A mammalian peptide present within the litorin/ranatensin-like family is neuromedin B.

A Sequence Identification of some of the sequence variations of Bombesin is included prior to the claims: e.g. Bombesin (ID#2), Gastrin Releasing Peptide (ID#1), Litorin (ID#3).

Herein, the term "bombesin or natural variant thereof" includes all subfamilies and natural variants of bombesin (ID#2)[See Falconieri, et.al. Regulatory Peptides, 21, 1–11, 3, (1988), for a listing of known Bombesin related peptides and is incorporated herein by reference] including sequences related to GRP (ID#1), and Litorin (ID#3) and the like. The term "variations thereof" for substituents $A_1$ and $A_9$ optionally includes 1–5 amino acids of bombesin or related variants contiguous with a consecutive region of the amino acids $A_2$ to $A_8$ as defined; unless it is a bond or unless the amino or carboxy terminal acid is a cyclic derivative and thereby the sequence of 1–5 amino acids is omitted.

Amino Acids & Modifications

Herein, as is customary, the structure of peptides when written is such that the amino terminal end appears on the left side of the page and the carboxy terminal end appears on the right side of the page.

An alkyl group of 1–8 carbon atoms and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl, heptyl, octyl(Oct), 8-aminooctanoic acid(Aoc). An acyl group of from 2 to 8 carbon atoms is taken to include straight, branched, cyclic, saturated and unsaturated acyl groups having 1 or 2 carbonyl moieties per group, for example, acetyl-(Ac), azetidine-2-carboxylate(Azt), benzoyl, succinyl, cinnamoyl(Cin), 3,4-dihydrocinnamoyl(DhCin), maleyl(Mal), palmityl, lauryl, octanoyl, and glutaryl(Glt). Both alkyl and acyl substituents are taken to include those groups with halogen substituents, where a halogen group is a fluoro, chloro, bromo or iodo, for example, trifloroacetyl(Tfa). Internally cyclized derivatives of N-terminal amino acid residues include pyroglutamic acid (pGlu) and homoserine lactone (Hse). Presence of a internally cyclized amino acid involving the N-amino group serves to terminate the peptide chain, thereby limiting the extension of the peptide chain and the presence of chemical substituents on the N-amino group.

The naturally occurring amino acids, with the exception of glycine, contain a chiral carbon atom. Unless otherwise specifically indicated, the optically active amino acids, referred to herein, are of the L-configuration. However, any of the amino acids of the $A_1$ or $A_9$ group can be specifically designated to be either the of the D- or L-configuration.

The amino acids of $A_1$ through $A_9$ essentially consists of the naturally occurring amino acids which are glycine, alanine, valine, leucine, isoleucine, serine, methionine, threonine, phenylatanine, tyrosine, tryptophan, cysteine, proline, histidine, aspartic acid, asparagine, glutamic acid, glutamine, arginine, ornithine, and lysine. Also included would be the D-isomers of the naturally occurring amino acids; D-alanine, D-valine, D-leucine, D-isoleucine, D-serine, D-methionine, D-threonine, D-phenylalanine, D-tyrosine, D-tryptophan, D-cysteine, D-proline, D-histidine, aspartic acid, D-asparagine, D-glutamic acid, D-glutamine, D-arginine. As indicated earlier, D amino acids may be represented by the first letter of their 3 letter or 1 letter code being a lower case letter; i.e for D-Alanine (ala, or a).

Groups of amino acids can be defined by certain charge characteristics. There are two general characteristics of side chains: nonpolar and polar. The nonpolar residues are made up of these groups: the hydrophobic residues which includes those with (1) aliphatic hydrocarbon side chains: Gly, Ala, Val, Leu, Ile, Nle, Pro and (2) the aromatic group Phe and Trp, and (3) the pseudohydrocarbon, Met. The polar amino acids are made up three groups: (1) The acidic hydrophobic residues Asp, Glu, and Tyr, (2) the neutral residues with the hydroxyl-containing residues, Ser and Thr; the amides, Asn and Gln; the aromatic rings, Tyr and Trp; the sulfhydryl groups, Cys, and small structurally accommodating amino acids Ala and Gly, and (3) basic hydrophobic residues His, Lys, and Arg.

Y designates the chemical group(s) that may be utilized to substitute or modify the terminal amino acid. Therefore, Y may be a carboxy terminal acid (—OH), $C_1$-$C_8$ alkoxyester, carboxamide, mono or di $C_1$-$C_8$ alkylester, $C_1$-$C_8$ alkylamine, or $C_1$-$C_4$ thioalkylether, or a pharmaceutically acceptable salt in addition or in conjunction with any of the substituents.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

It is understood amino acids containing the methyl sulfides and the methyl amides existent herein are designated ($\Psi[CH_2S(CH_3)]$) and ($\Psi[CH_2N(CH_3)]$) respectively. Utilizing conventional nomenclature employed by peptide chemists, $A_8$-$\Psi$-$A_9$ are those compounds wherein the moiety connecting the two amino acids $A_8$ and $A_9$ is by a modified peptide linkage; such as by a methylene methyl sulfide or methylene methyl amide bond. For example, where the $A_8$ residue is Phe linked to the $A_9$ Leu residue by a methylene methyl sulfide or methylene methyl amide bond, they can be designated respectfully as Phe$\Psi[CH_2S(CH_3)]$Leu and Phe$\Psi[CH_2N(CH_3)]$Leu. This designation indicates that the carbonyl group of the penultimate Phe is reduced to a methylene which is bonded to the methyl sulfide group or methyl amide group of The $A_9$ substituent respectively.

The procedure to prepare starting materials of formula 1 wherein $\Psi$ is a —$CH_2S(CH_3)$— group, that is the $\Psi[CH_2S]$ compounds, is known from Spatola, A. F. and Edwards, J. V., Biopolymers, 25, S229–S244 (1986), hereby incorporated by reference, and Spatola and Darlak, Tetrahedron Letters, 44(3), 821-33 (1986), hereby incorporated by reference. Similarly the procedure to prepare starting materials of formula 1 wherein $\Psi$ is a —$CH_2N(CH_3)$— group, that is the $\Psi[CH_2N(CH_3)]$ compounds, is known from Sasaki and Coy, Peptides 8, 119-121 (1986), hereby incorporated by reference.

Synthesis of compounds having modified dipeptide substituents of the structure $A_8$-$\Psi[CH_2S(CH_3)]$-$A_9$ can be obtained (scheme 1). The modified dipeptides of scheme 1 are obtained by initially preparing the modified amino acids shown as Generic Compound 1 and Generic Compound 2.

REACTION SCHEME 1

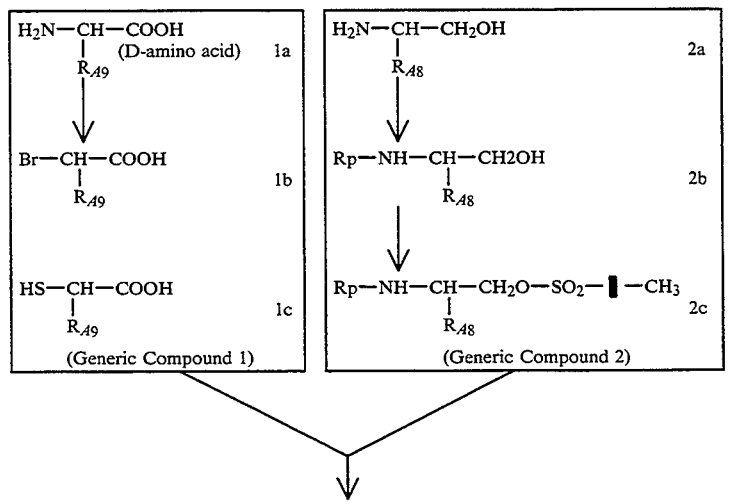

REACTION SCHEME 1

-continued

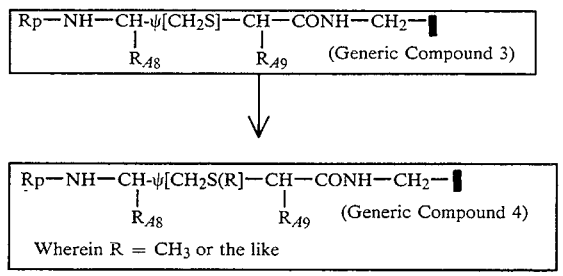

The Generic Compound 1 is obtained by starting with a D-amino acid having a $R_{A9}$ group (1a). $R_{A9}$ designates structures of desired amino acid of 1a when taken as a substituent with the α-amino acid. Suitable protection of reactive groups present on the $R_{A9}$ substituent can optionally be selected. Such selection for $R_{A9}$ protection is described in the literature and are well known to those skilled in the art. To synthesize Generic Compound 1, the D-amino acid 1a is first halogenated to produce the α-halo $R_{A9}$ substituted acid 1b. The α-bromo $R_{A9}$ substituted acid 1b can suitably be formed using potassium bromide in aqueous sulfuric acid. The α-halo $R_{A9}$ substituted acid 1b can then be converted to the a-mercapto $R_{A9}$ acid by treatment with salts of mercaptans (e.g. thiolate ions). A suitable method for forming α-mercapto $R_{A9}$ acid is reaction with sodium trithocarbonate, followed by workup of the reaction product to afford the α-mercapto, $R_{A9}$-alkanoic acid 1c.

Generic Compound 2 can be obtained by starting with an L-α-amino $R_{A8}$-substituted alcohol 2a. The a-amino group can then be suitable protected for peptide synthesis, as is well known in the art. Suitable protection can be afforded by the di-t-butyloxycarbonate (Boc) protecting group to form, for example, the Boc-amino-$R_{A8}$-substituted alcohol 2b, where it is understood Boc is a suitable substituent for Rp. The alcohol functionality of 2b can then be activated to a suitable leaving group, as in 2c, for condensation with Generic Compound 1c. The formation of the tosylated (—SO$_2$— ▮ —CH$_3$) leaving group present in 2c has been found to be suitable for reaction with the generic compound 1 for condensation.

The Generic Compound 3 is obtained by reacting the Generic compound 1c with Generic Compound 2c resulting in the substitution of the sulfide and displacement of the tosylate group. This can suitably be done by reacting Generic Compound 1c with with sodium ethoxide to preform the disodium of salt of the mercaptoacid and then react the mercaptoacid salt with Generic Compound 2c, displacing the tosyl group to form the dipeptide of Generic Compound 3. Compounds of the structure 3 can be optionally linked to a resin support (▮), by methods known in the art and described herein.

Generic Compound 3 then can be conveniently converted to the methyl sulfide of Generic Compound 4. Methylation of the sulfide can done with a number of methylating reagents. A suitable means of accomplishing this step is to react the generic compound 3 with iodomethane to form the sulfur-ylide for isolation. Methylation of compounds of the structure 4 can be optionally linked to a resin support (▮). Similarly, methylation of the dipeptide linkagae can be done before or after synthesis of the desired peptide sequence on the support, however, it is generally preferred to be done after the desired sequence has been completed.

Synthesis of compounds having modified dipeptide substituents of the structure $A_8$-Ψ[CH$_2$N(CH$_3$)]-$A_9$ can be generally be obtained (scheme 2).

REACTION SCHEME 2

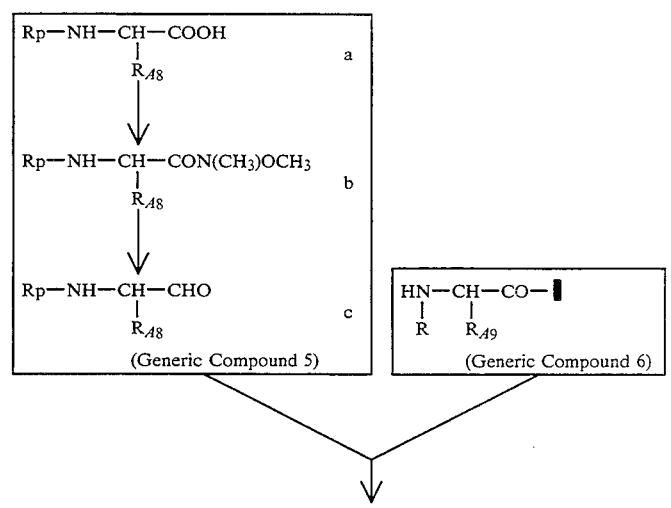

REACTION SCHEME 2 -continued

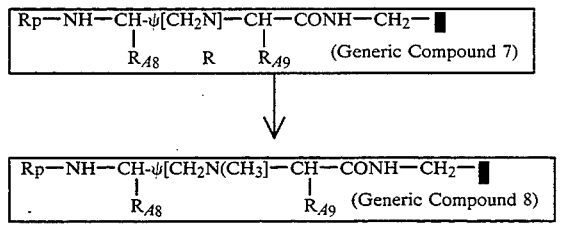

The modified dipeptides of scheme 2 are obtained by initially preparing the modified amino acids shown as Generic Compound 5 and Generic Compound 6.

α-(Acylamino) and a-(alkoxycarbonylamino) aldehydes of Generic Compound 5c can be prepared by oxidation of N-protected amino alcohols or by reduction of amino acids or their esters 5b with diisobutylaluminum hydride. For example, suitably the α-(t-butoxycarbonylamino)-aldehydes can be prepared from the corresponding N-methoxy-N-methylcarboxamides by reduction with lithium aluminum hydride when Rp is designated as $CH_3$ or the like. The N-methoxy-N-methylamides can be prepared by reaction of the α-(t-butoxycarbonylamino) acids with O,N-dimethylhydroxylamine hydrochloride in the presence of triethylamine and the coupling reagent benzotriazol-1-yloxytris[dimethylaminophoshonium hexafluorophospate (BOP). Reduction of 5b with lithium aluminum hydride gives the lithium salt of of compound 5c.

Compound 5 (optionally bound to a support resin) and Compound 6 can be reacted in aqueous solution to form the shiff base between the amine and the aidehyde, which can be subsequently reduced. Suitable reduction of the shiff base can be carried out with sodium borohydride (or derivative thereof) to form the Generic Compound 7. The structure of compound 7 can be suitable methylated as described for Generic Compound 4.

Specifically, Compounds of 5c can be prepared by reducing the N-methoxy-N-methylamide of formula 5b to produce the aldehyde of formula 5c.

pound in a nonreactive solvent such as an ethereal solvent such as tetrahydrofuran (THF) or diethylether. After the reaction is substantially complete, typically after about 30 minutes, the reaction mixture is quenched by the addition of, for example, 10% potassium or sodium hydrogen sulfate and then water. The product 5c can then be isolated by, for example, extraction of the aqueous mixture with a solvent such as diethylether, washing the ether phase with cold, dilute aqueous hydrochloric acid, drying and solvent removal. The crude product can be purified by, for example, column chromatography such as a silica gel column eluting with 55% ethyl/acetate/hexane.

The N-methoxy-N-methyl amides of formula 5b can be prepared from the corresponding N-Boc protected acid in the usual manner. Carbonyldiimidazole is added to a dried solution of the N-Boc protected amino acid in an ethereal solvent such as diethylether. The reaction mixture is allowed to stir for from 10 minutes to 1 hour, typically for about 15-20 minutes. N,O-dimethylhydroxylamine HCl in DMF and a sterically hindered amine such as diisopropylethyl amine is added and the mixture allowed to stir for from about 6 hours up to about 24 hours at room temperature. The desired compound is then isolated by solvent evaporation and crude purification can be accomplished by, for example, flash chromatography on silica gel eluting with methylene chloride.

The formula 5c aldehyde is then reacted with a resin-bound amino acid of formula 6 to form a Schiff base adduct

METHOD A

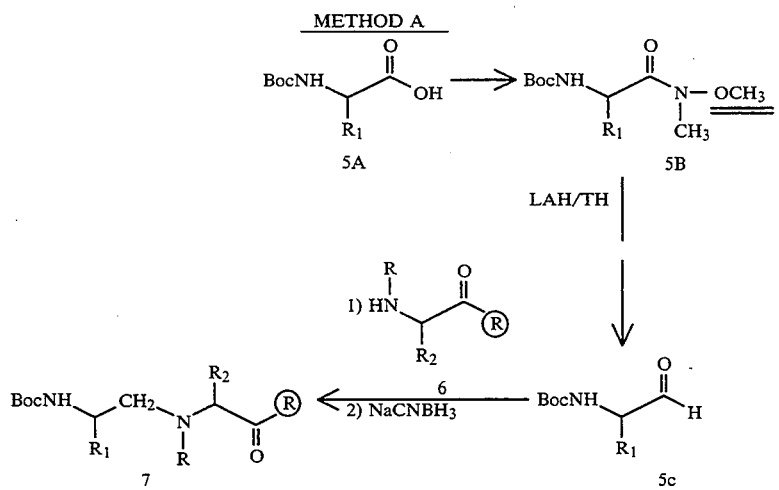

The reduction can be performed in any way generally known and readily performed by those skilled in the art such as by use of lithium aluminum hydride ($LiAlH_4$). This reduction can be conveniently carried out by adding about one molar equivalent of $LiAlH_4$ to a cooled, typically about 0° C., solution of a formula 5A com-

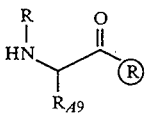

wherein R is methyl and $R_{A9}$ are as defined for formula 1 and wherein; ⓡ resents the resin. The schiff base adduct r is then reduced in situ, for example, by sodium cyanoborohydride, to give a resin bound modified dipeptide of formula 7

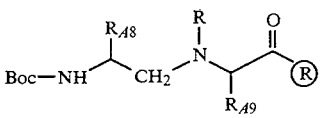

wherein R, $R_{A8}$ and $R_{A9}$ are as defined for formula 1 and wherein ⓡ represents the resin.

Methods of reacting compounds of formula 5c with a amino acid of formula 6 on a resin support, through Schiff base formation and subsequent reduction to give modified dipeptides of formula 7, are preferred when R is hydrogen or methyl.

Alternative methods (Method B) of making the compounds of formula 5, wherein R is methyl, ethyl, propyl, isovaleryl, or like alkyl substituent of 1-5 carbon atoms, or phenylalkylidene, can be performed by reductive alkylation. Specifically, compounds of formula 7 wherein R is hydrogen can be subjected to a subsequent reaction with with compounds of the formula 7A to produce the modified dipeptide of formula 8, wherein the subsequent R group is derived from the substituted alkyl group (represented as $X_1$ and a functional aldehyde group).

The alternative method (method B) first reacts a formula 7A aldehyde with the resin bound dipeptide of formula 7, wherein R is a hydrogen group and the circled R

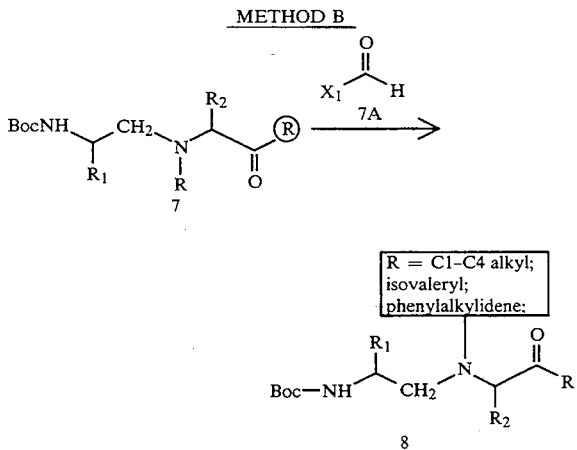

represents the resin. The initially formed Schiff base adduct is then reduced in situ using, for example, sodium cyanoborohydride to give a resin bound dipeptide of formula 8. The $A_7$ through $A_1$ amino acids can then be sequentially added to the resin bound modified dipeptide in the usual manner.

The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced G-amino protected amino acid.

An example of a hydroxymethyl resin is described by Bodanszky, et al., Chem. Ind. (London) 38, 1597–98 (1966). A chloromethylated resin is commercially available from Bio Rad Laboratories, Richmond, Calif., and the preparation of such a resin is described by Stewart and Young, "Solid Phase Peptide Synthesis" (Freeman & Co., San Francisco 1969), Chapter 1, pp. 1–6. The protected amino acid can be bound to the resin by the procedure of Gisin, Helv. Chem Acta, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Peptide Synthesis

The peptides of formula 1 of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide synthesizer. Peptides of formula 1 were synthesized on the resin beginning with a protected dipeptide containing a either a inter-amino acid methylene methyl sulfide or a methylene methyl amide bridge with the C-terminal amino acid of the dipeptide attached to a methylbenzhydrylamine resin. Peptides of formula 2 traditionally have the carboxy terminal amino acid attached to a methylbenzhydrylamine resin for subsequent extension. The extension of the peptide sequence was done using standard methodology and that of the manufacturer and that known by people skilled in the art. Extension of the peptide chain is by coupled amino acids is known for both L and D isomers of amino acids.

After completion of coupling of the sequence either the Boc protecting group was left in place or it was removed and the N-terminal amino group alkylated or acylated using those methods known in the art. After the desired N-terminus is formed then displacement of the protecting groups and removal of the peptide from the resin is accomplished using a hydrogen fluoride solution, as known in the art.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzylcarbonyl, p-bromobenzyloxycarbonyl, p-methoxybenzyloxycarbonyl, 1-(p-biphenylyl)-1-methylethoxycarbonyl, α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thiourethane type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl (Boc).

As is known in the art of solid phase peptide synthesis many of the amino acids bear functionalities requiring protection during synthesis. The use and selection of the appropriate protecting group will depend upon the amino acid to be protected and the presence of other protected amino acid residues on the peptide. Generally, the selection of such a side chain protecting group requires that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl. The selection and use of appropriate protecting groups for each peptide is within the ability of those skilled in the art.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyldi-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc—Ala—O—Ala—Boc), (8) nitrogen containing heterocyclic compounds having a hydroxy group on one ring nitrogen (e.g., N-hydroxyphthalimide, N-hydroxysuccinimide and 1-hydroxybenzotriazole), and (9) diphenyl phosphorylazide. Other activating reagents and their use in peptide coupling are described by Kapoor, J. Pharm. Sci., 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a fourfold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

After the desired amino acid sequence has been obtained, the peptide is removed from the resin. This can be done by hydrolysis such as by treatment of the resin bound polypeptide with an amino acid alcohol and acetic acid in dichloromethane (DCM). Protecting groups can also be removed by other procedures well known in the art. Typically protecting group removal is done after the peptide chain synthesis is complete but the protecting groups can be removed at any other appropriate time. Purification of peptides is principally accomplished through preparative reverse phase high performance liquid chromatography and those techniques known to those skilled in the art.

The ability of the peptide derivatives of this invention to act as agonists or antagonist of Bombesin can be demonstrated by the ability of such peptides to compete with radioiodinated bombesin/GRP for mammalian bombesin/GRP receptors using the method of Buck, et al., *Science* 226: 987–989, 1984, and by the ability of such compounds to stimulate bombesin induced phosphatidylinositol turnover using the method of Bristow, et al., *British J. Pharmacol.* 90: 211–21, 1987.

THERAPEUTIC USE

Stimulating/Inhibition of Digestion

Specific pharmacological effects of bombesin analogs to stimulate digestion have been elicited by systemic injection. For example, intravenous injection of bombesin analogs is able to stimulate gastric acid secretion [reviewed in Walsh, J., Annu. Rev. Physiol. 50, 41–63, (1988)]. Both peripheral and central administration of bombesin peptides delays the gastric emptying while also stimulating gastrointestinal smooth muscles in vitro. It has also been demonstrated, for example, exogenous administration of bombesin induces the release of both gastrin and somatostatin in isolated vascularly perfused rat stomachs. Similarly guinea pig antrum logitudinal muscle strips directly stimulate the frequency of spontaneous contractions and direct the contraction of the muscularis mucosase of the colon. However, it is to be noted that these effect may not occur if their administration is to the brain or spinal cord. The applicants use of the peptide to stimulate/inhibit digestion, are therefore, useful when those effects are consistent with the necessary mechanisms of digestion and are consistent with peripheral administration (i.e., not being injected into the brain or spinal cord).

The natural history of peptic ulcer disease is one of recurrent exacerbations and remissions. As a result, ulcerative diseases should be treated as a chronic disorder. Peptic (esophageal, gastric, and duodenal) ulcers occur in areas of the gastrointestinal tract exposed to acid and pepsin. The compounds of the present invention which are antagonist of the bombesin receptor may be useful in the treatment of gastrointestinal and/or pancreatic ulcers and may be effective in resultant hypersecretions occurring from the pancrease and/or stomach, particularly hydrochloric acid and pepsin. As such compounds of this invention may serve as an appropriate intervention to treat peptic ulcers.

Stimulation/Inhibition of Growth

Binding of Bombesin to its cell surface receptor elicts cell mitogenic responses in a number of tissues. The initial demonstration that the bombesin peptides could function as mitogens was demonstrated on Swiss 3T3 murine embryonal fibroblasts [Rozengurt and Sinnett-Smith, BBRC 140, 379-385 (1983)]. Latter studies by Represa [Represa J. J., et. al. Development 102, 87-96 (1988)] showed that bombesin could reactivate cell division and development in growth-arrested occular vesicles. Similar increases in the clonal growth rate and colony-forming efficiency were observed by Willey et. al. 1984 for GRP and GRP analogs [Willey, J. C., et al., Exp. Cell Res 153, 245-248 (1984)]. A number of groups have observed the presence of high-affinity receptors for bombesin/GRP in a number of human small cell lung carcinomal cell lines and showed bombesin could elevate levels of thymidine incorporation with peptides added to the media [See Weber et al., J. Clin. Invest 75, 306-309 (1985); Carney, et al., Cancer Res. 47, 821-825, (1987)]. A measurable effect on gastrin cells in the antral mucosa of the rat stomach were noted by [Lehy et. al., Gastroenterology, 84, 914-919 (1983)] following the administration of bombesin. Chronic treatment of the bombesin has also been shown to induce a dose-dependent pancreatic cell hypertrophy (Lhoste et al. 1985a). The applicants use of the peptide to stimulate growth, are therefore, useful when those effects are consistent with the necessary mechanisms of growth and are consistent with the effects seen with peripheral administration.

Use of bombesin antagonist in cancer therapy is indicated for the treatment of small cell lung carcinomas (SCLC) and prostatic carcinomas and prevention of a variety of other cancer conditions. Those experienced in this field are readily aware of the circumstances requiring cancer therapy.

As used herein, the term "tumor tissue" means both benign and malignant tumors or neoplasms and includes melanomas, lymphomas, leukemias, and sarcomas. Illustrative examples of tumor tissues are cutaneous such as malignant melanomas and mycosis fungoides; hematologic tumors such as leukemias, for example, acute lymphoblastic, acute myelocytic, or chronic myelocytic leukemia; lymphomas such as Hodgkin's disease or malignant lymphoma; gynecologic tumors such as ovarian and uterine tumors; urologic tumors such as those of the prostate, bladder, or testis; soft tissue Barcomas, osseus, or non-osseous Barcomas, breast tumors; tumors of the pituitary, thyroid, and adrenal cortex; gastrointestinal tumors such as those of the esophagus, stomach, intestine, and colon; pancreatic and hepatic tumors; laryngeae papillomestasas and lung tumors.

The term "controlling the growth" and the concept of treating a cancer means slowing, interrupting, arresting, or stopping the growth and metastases of a rapidly proliferating tumor in a warm blooded animal; it being understood that treatment in a warm blooded animal does not generally provide a "cure" for the tumor in the sense that necessarily the tumor tissue is destroyed or totally eliminated.

Therapeutic Administration

The appropriate dose of a peptide derivative of this invention when used in the treatment of patient in need thereof is from 0.2 mg/kg to 250 mg/kg of patient body weight per day depending on other factors involving the particular patient and the peptide derivative selected. The suitable dose for a particular patient can be readily determined. Preferably from 1 to 4 daily doses would be administered typically with from 5 mg to 100 mg of active compound per dose. The amount of a peptide of this invention required can be readily determined by those skilled in the art.

The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

As pharmacologically useful agents, compounds of formula 1 can be administered in various manners to the patient being treated to achieve the desired effects, such that, the compounds can be administered either alone or in combination with one another, or they can be administered. Specifically, compounds of formula 1 may be useful is combination with standard radiological and or chemical treatments in cancer therapy, whereby the the compounds are expected to increase the effectiveness of said radiological or chemical treatments existing in the field. As used herein, the term "conjunctive administration" when used in relation to the administration of compounds of formula 1 means the administration of such compound during the time in which the patient requires such need treatment as medically determined.

EXAMPLES

This invention is illustrated by the following, nonlimiting examples.

Example 1

Preparation of $A_8\Psi[CH_2S(CH_3)]A_9$Litorin

2-Mercapto-4-Methylpentanoic Acid (Compound 1)

A solution of D-Leucine (5 g) and potassium bromide (114 g) in 400 ml of 2.5 N $H_2SO_4$ was cooled to $-5°$ C. in an ice salt bath. A cold solution of $NANO_2$ (30 g/70 ml water, 0°–50° C.) was added dropwise with stirring. The reaction was allowed to proceed for ~14 hours at room temperature. The reaction was then extracted with 75 ml portions of ether three times. The ether extract was dried over anhydrous sodium sulfate. The solution was filtered and the ether was evaporated. The resulting clear oil, 2-bromo-4-methylpentanoic acid (Martin and Greco, (1968) J. Org. Chem. 33, 1275–1276) (18 g) was committed to a 250 ml solution of 33% sodium trithiocarbonate with stirring at 0° C. The reaction was stirred for 48 hrs and then acidified at 0° C. with judicious addition of 10N $H_2SO_4$. The acidified solution was then extracted with 75 ml portions of ether three times. The ether extracts were dried over anhydrous sodium sulfate, and subsequently the ether was removed in vacuo. The resulting yellowish oil (17 g) was vacuum distilled. The final yield was 15.3 g of (S)-2-mercapto-4-methylpentanoic acid; b.p. 92–93 (0.75 mmHg); $[\alpha]_D 25 = -23.2$ (cl,MeOH).

(S)-(tert-Butyloxycarbonyl)-2-Amino-3-Phenyl-Propanyl-p-Toluenesulfonate (Compound 2)

The starting reagent for the title compound, was synthesized from (S)-(tert-Butyloxycarbonyl)-2-amino-3-Phenyl-Propanol(4.5 g, 0.0179 moles; prepared from L-phenylalanino (Sigma) and di-tert-butyldicarbonate). The starting reagent was then added to 20 mls of pyridine under anhydrous conditions and chilled to $-40°$ C. in a dry ice/acetone bath. To the mixture tosyl chloride was then added (6.9 g, 3.6 mmol). The reaction mixture was then run at 4° C. No effort was made to remove accumulating deposits of pyridinium chloride. Upon termination of the reaction, the pyridine was removed in vacuo, and the resulting solid was exacted in ether. The ether extract was dried over anhydrous sodium sulfate, filtered, and the ether removed in vacuo; yielding 10.5 g of a oil. Crystals of the product were obtained from precipitation of the oil in ethyl acetate and hexane; yielding 9.0 g of a white solid; m.p., 109–110° C.

(S)-(S)-tert-Butyloxycarbonyl-Phe$\Psi$[CH_2S]Leu-OH (Compound 3)

A 0.43 M solution of sodium ethoxide (Solution A) was prepared with freshly cut sodium and anhydrous ethanol. An ethanol solution of Compound 1, (S)-2-mercapto-4-methylpentanoic acid (0.72 g in 25 mls), (solution B), was prepared. A 13.5 ml volume of solution A was slowly added to 15 ml of solution B under nitrogen atmosphere. The solution was stirred for five minutes, and the ethanol removed in vacuo, and the white solid repeatedly evaporated with benzene until dry. The resulting disodium salt of mercaptoleucine was dissolved in ~1 ml of dimethylsulfoxide (DMSO) to which was added 1.58 g of compound 2 dissolved in 2 mls of DMSO, and stirred overnight. The reaction mixture was combined with 175 ml of distilled water and extracted with 20 ml portions of ether three times and then acidified with 5N HCl with stirring at 0° C. The aqueous solution was re-extracted 3X with ethyl acetate. The extract was washed with a saturated NaCl solution and dried over sodium sulfate, filtered, and the ethyl acetate removed in vacuo yielding 1.05 g of a clear oil. This was crystallized from ethyl acetate and hexane; yielding a white solid; (0.83 g), (mp, 110–111), ($[\alpha]25 = 52.5$ (C0.88 l, MeOH)).

S)-(S)-tert-Butyloxycarbonyl-Phe$\Psi$[CH_2S]Leu-resin(-Compound 4)

The resins utilized in solid phase peptide synthesis are prepared such that the alpha carboxyl group of the C-terminal amino acid residue is covalently attached to the resin matrix. Although many support resins are known in the field, peptide synthesis is generally conducted in a reaction vessel on an insoluble resin support, generally with a styrene-1%-divinylbenzene polymer. The carboxy-terminal amino acid is often attached to the resin by a special organic linker, however, direct attachment to the resin is well known in the field. For example, resins with suitable organic linkers are the 4-(oxymethy)phenylacetamidomethyl (PAM) resin or the p-benzyloxybenzyl alcohol (WANG) resin.

Compound 3 was attached to a methyl benzhydramine resin by activating compound 3 (converted to the active ester) with hydroxybenzotriazole in acetonitrile/dimethylacetamide and dicyclohexylcarbodiimide in acetonitrile.

[Phe$_8\Psi$[CH_2S]Leu$_9$]Litorin (Compound 5)

The solid phase peptide synthesis for elongation of the designated amino acid sequence was performed on an Applied Biosystems peptide synthesizer using standard methodology, that of the manufacture, and that known by people skilled in the art.

The completed resin bound peptide was cleaved from the resin employing hydrogen fluoride at 0° C. in the presence of anisole (ethanedithiol) for 1 hr. Following, removal of the HF the resin was stirred and extracted with diethyl ether (2×30 ml) and extracted with 30% acetic acid. Lyphilization afforded crude product. A portion of the product was purified on preparative reverse phase high performance liquid chromatography with a C18 Dynamax column employing a mobile phase gradient elution (acetonitrile gradient; established from reservoirs of acetonitrile and 0.1% TFA in water). Fractions of the principle peak were collected monitoring absorbance of the compound at $A_{214}$.

[Phe$_8\Psi$[CH_2S(CH_3)]Leu$_9$]Litorin (Compound 6)

A sample of the [Phe$_8\Psi$[CH_2S]Leu$_9$]Litorin (5 mg) was stirred in 5 ml of iodomethane for one hour and the iodmethane was removed via evaporation to give the sulfur ylide. The resulting product was further purified on preparative reverse phase high performance liquid chromatography with a C18 Dynamax Column employing a mobile phase gradient (15 min acetonitrile gradient 5–15% at 40 ml/min; established from reservoirs of acetonitrile and 0.1% TFA in water].

Example 2

[t-Butyloxycarbonyl]-L-Leucine N-Methoxy-N-methylamide: Compound (7)

Triethylamine (10 ml) is added to a stirred solution of Boc-Leucine in dichloromethane. Then sequentially, carbonyl-diimidazole (10 mmol) are added followed by, N-dimethylhydroxyamine hydrochloride (11 mmol), and triethylamine (11 mmol). The reaction is monitored by TLC, was found to be completely within an hour.

The mixture is diluted with dicloromethane (250 ml) and washed successively with 1N HCl, and a saturated sodium chloride solution. The organic solution was dried with magnesium sulfate, and the solvent evaporated to give the desired product (9.0 mmol yield).

(t-Butyloxycarbonyl)-L-Leucinal: Compound (8)

Lithium aluminum hydride (2.5 equiv.) is added to a stirred solution of compound (7). Reduction is complete within 15-20 minutes. The mixture is hydrolyzed with a solution of potassium hydrogen sulfate in water. Ether is added and the aqueous phase is separated and extracted. The organic phases are combined, washed with 1N HCl saturated sodium hydrogen carbonate and saturated sodium chloride, and dried with magnesium sulfate. The solvent is evaporated to leave the desired product

[Phe$_8\Psi$[CH$_2$N(CH$_3$)]Leu$_9$]Litorin: (Compound 9)

Compound (8) was reacted with TFA-H-Leucinyl-p-methylamine resin (1% cross-linked) in 1% acetic acid in DMF for 3 hours using NaBH$_3$CN (25 equivalents). The reaction was found to be complete based on the Kaiser test.

The solid phase peptide synthesis for elongation of the amino acid sequence was performed on an Applied Biosystems peptide synthesizer using standard methodology, that of the manufacture, and that known by people skilled in the art.

The peptides obtained by this method gave the desired molecular ion peak by FAB-MS and had an amino acid analysis in accordance with the desired peptide. In this way the following peptides having the stated properties were prepared.

(ID#9)  pGlu Gln Trp Ala Val Gly His Phe$\Psi$[CH$_2$S(CH$_3$)]Leu-NH$_2$
MW 1084

(ID#8)  pGlu Gln Trp Ala Val Gly His Phe$\Psi$[CH$_2$N(CH$_3$)]Leu-NH$_2$
MW 1066 FAB-MS (MH+) 1057 t$_R$
60% peptide content Example 4

Binding to the Bombesin Receptor as Demonstrated by Iodinated GRP

Figure 2:
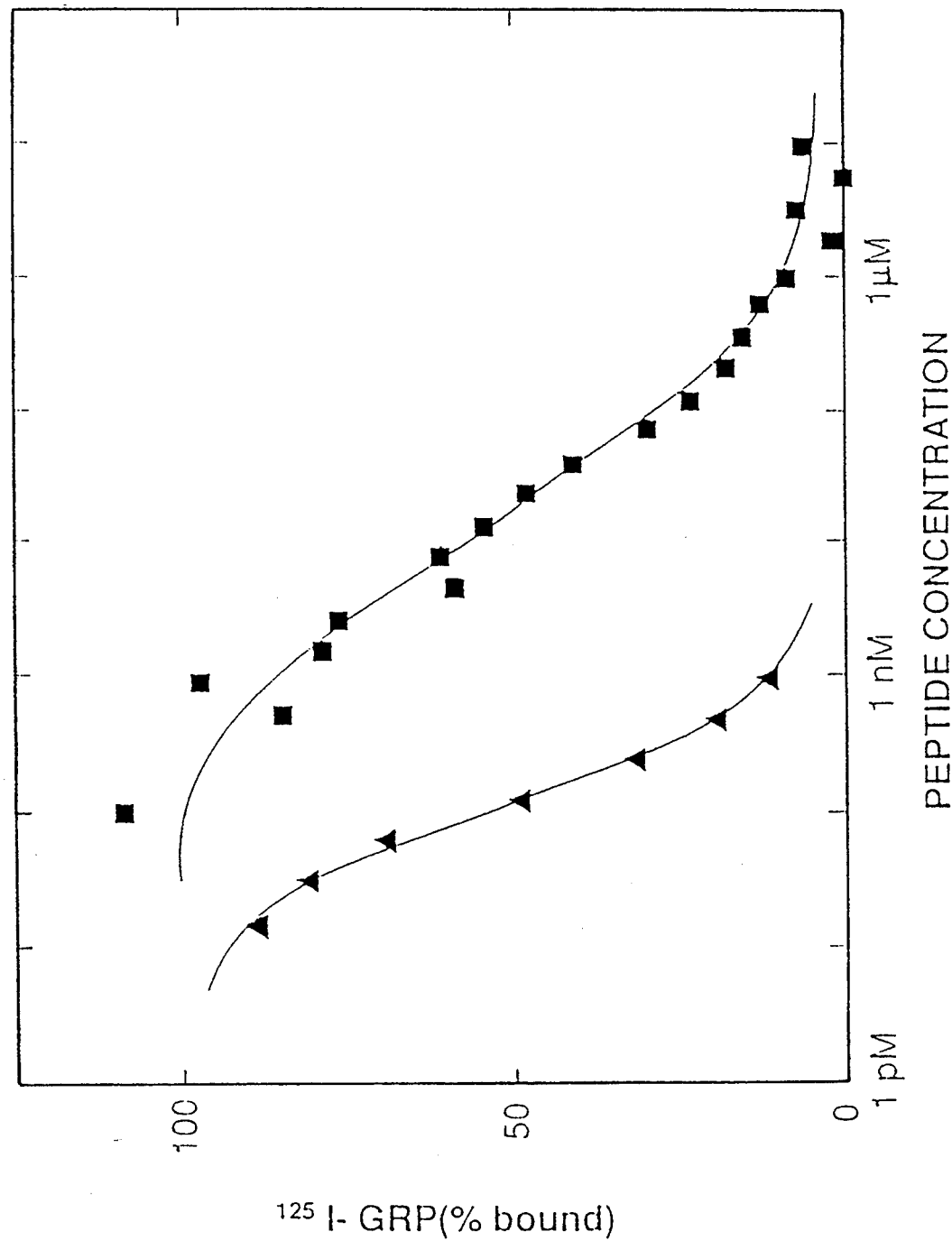
FIG. 2 illustrates the ability of bombesin analogs to bind to the GRP receptor as demonstrated by the ability of these peptides to compete for binding of $^{135}$I-GRP to murine pancreatic membranes (Example I).

The pancreata from one or more mice were pooled and homogenized in 50 mM HEPES (pH 7.4) containing 120 mM NaCl, 5 mM KCl, 1 mM EDTA and protease inhibitors (1 µg/ml aprotinin, leupeptin, pepstatin; 4 µg/ml bacitracin, antipain, bestatin; 100 µM PMSF) at 4° C. and centrifuged at 37,500 X g for 15 minutes. The pellet was resuspended in 50 mM HEPES (pH 7.4) containing 10 mM EDTA, 300 mM KCl, and protease inhibitors, and then incubated for 30 minutes at 4° C. The suspension was centrifuged as above and the pellet was washed two times in 50 mM HEPES (pH 7.4) containing 8 µg/ml thiorphan and protease inhibitors, and again centrifuged. The tissue was then resuspended in incubation buffer (1 ml per 4 mg pancreas) and incubated for 15 minutes at room temperature, then 250 µl were added to each assay tube to commence the assay. The assay tubes contained incubation buffer consisting of 50 mM HEPES (pH 7.4), 0.5% BSA, protease inhibitors, 2 mM MnCl$_2$, 8 µg/ml thiorphan, 1 µM somatostatin, and concentrations of $^{125}$I-GRP and peptides as needed in a final volume of 500 µl. The assay was allowed to proceed to equilibrium for 90 minutes at room temperature. After this time, the contents of each tube was rapidly filtered over Whatman GF/B filters pre-soaked in 0.1% polyethyleneimine and the filters were rapidly washed three times with ice-cold 50 mM HEPES (pH 7.4). Filter-bound radioactivity was quantitated in a gamma counter. Competition of iodinated GRP binding by test compounds or standards was expressed as a percentage of $^{125}$I-GRP binding in the absence of peptide. Affinity and maximal binding were calculated with LIGAND (Biosoft, Cambridge, UK) (FIGS. 1 and FIG. 2)

Example 5

Effect of Analogs on the Bombesin Receptor as Demonstrated by Phosphatidylinositol Turnover Pancreata from mice were chopped at 350 µm with a tissue chopper and pooled. The chopped tissue was washed twice with oxygenated Krebs-Hepes, then incubated for 30 minutes in 37° C. oxygenated Krebs-Hepes buffer with fresh buffer after 15 minutes. The tissue was then incubated in this buffer containing 200 µCi of [$^3$H] inositol at 37° C. for 1 hour. The tissue was then washed twice and incubated for another 30 minutes in oxygenated Krebs-Hepes (containing 10 mM Li+) at 37° C. with a fresh buffer change after 15 minutes. Portions of the tissue mass (approximately 10 mg per assay tube) were then placed in Li+ buffer with protease inhibitors, (40 µg/ml bacitracin, 4 µg/ml leupeptin, 4 µg/ml chymostatin, 8 µg/ml thiorphan), 0.1% BSA, and 0.1-10 µM peptide in a final volume of 250 µl. After 60 minutes at room temperature, the phosphatidylinositol turnover was terminated by the addition of 940 µl chloroform:methanol (1:2), followed by 310 µl chloroform, followed by 310 µl water. Each tube was then vortexed for 5 seconds and then centrifuged at 2500 x g for 10 minutes to separate the phases. 50 µl of the bottom phase (chloroform) was withdrawn from each tube and placed in a counting vial, dried, and counted in scintillation fluid. 900 µl of the top (aqueous) phase were then mixed with 2.1 ml water and loaded onto a 0.5 ml Biorad AG-1X8 (formate) ion exchange column. The material on the columns was washed in order with: 1) 10 ml of water 2) 5 ml of 5 mM disodium tetraborate/60 mM sodium formate 3) 10 ml of 1 M ammonium formate in 0.1 M formic acid. The final (third) wash was collected and one ml was mixed with 14 ml of Bio-Safe scintillant and counted. The ratio of these counts (total inositol phosphates) to the corresponding organic phase counts (inositol incorporated into the tissue) was then calculated for each sample. The ratios in the presence of test compound and/or standards were then compared to the ratios for control tubes (i.e., no stimulating agonist). The abilities of test compounds to stimulate phosphatidyl-inositol turnover were determined with the aid of a computer program.

Explanation of Figures

FIG. 1 illustrates that $^{125}$I-GRP binds to a single class of sites-the bombesin/GRP receptor—on murine pancreatic membranes (Example 1). Binding of 25-1600 pM $^{125}$I-GRP was assayed in triplicate, then analyzed and plotted with LIGAND. The best computer fit of these data is 19 pM receptor per sample (~100 fmol receptor per mg membrane protein) with a Kd of 47 pM. The abscissa (x-axis) indicates the concentration of $^{125}$I-GRP bound to the receptor. The ordinate (y-axis) indicates the concentration of 125I-GRP bound to the receptor divided by the concentration of $^{125}$I-GRP that is free (not bound). The straight line is indicative of a single class of sites; that is, $^{125}$I-GRP binds to each of its receptors with the same affinity. Other experiments using 25-3200 pM $^{125}$I-GRP or 10 pM $^{125}$I-GRP±8-500 pM GRP also indicated a similar Kd. This shows that binding to the receptor for bombesin/GRP can be measured with $^{125}$I-GRP and murine pancreatic membranes.

FIG. 2 illustrates the ability of bombesin analogs to bind to the GRP receptor as demonstrated by the ability of these peptides to compete for binding of $^{125}$I-GRP to murine pancreatic membranes (Example 1). The abscissa (x-axis) logarithmically indicates the concentration of agonists being tested. The ordinate (y-axis) indicates the observed binding for each tested peptide measured as a percentage of maximal $^{125}$I-GRP binding (no peptide present). Binding of litorin (▲) was assayed in triplicate at the indicated concentrations in the presence of 40 pM $^{125}$I-GRP. Litorin binding best fit a single class of sites with a Kd=0.1 nM. Binding of (Phe$^8$Ψ[CH$_2$N(CH$_3$)]Leu$^9$)litorin (■) was assayed in duplicate at the indicated concentrations in the presence of 20 pM $^{125}$I-GRP. Two such curves were co-analyzed with $^{125}$I-GRP saturation curve (not shown) similar to that in FIG. 1: all three curves were from the same experiment. (Phe$^8$Ψ[CH$_2$N(CH$_3$)]Leu$^9$)litorin binding best fits two classes of sites (Kd=0.08 and 16 nM) with 20% of the receptors in the high affinity state. Analysis of several other litorin and (Phe$^8$Ψ[CH$_2$N(CH$_3$)]Leu$^9$)-litorin experiments have produced similar results.

Figure 3:
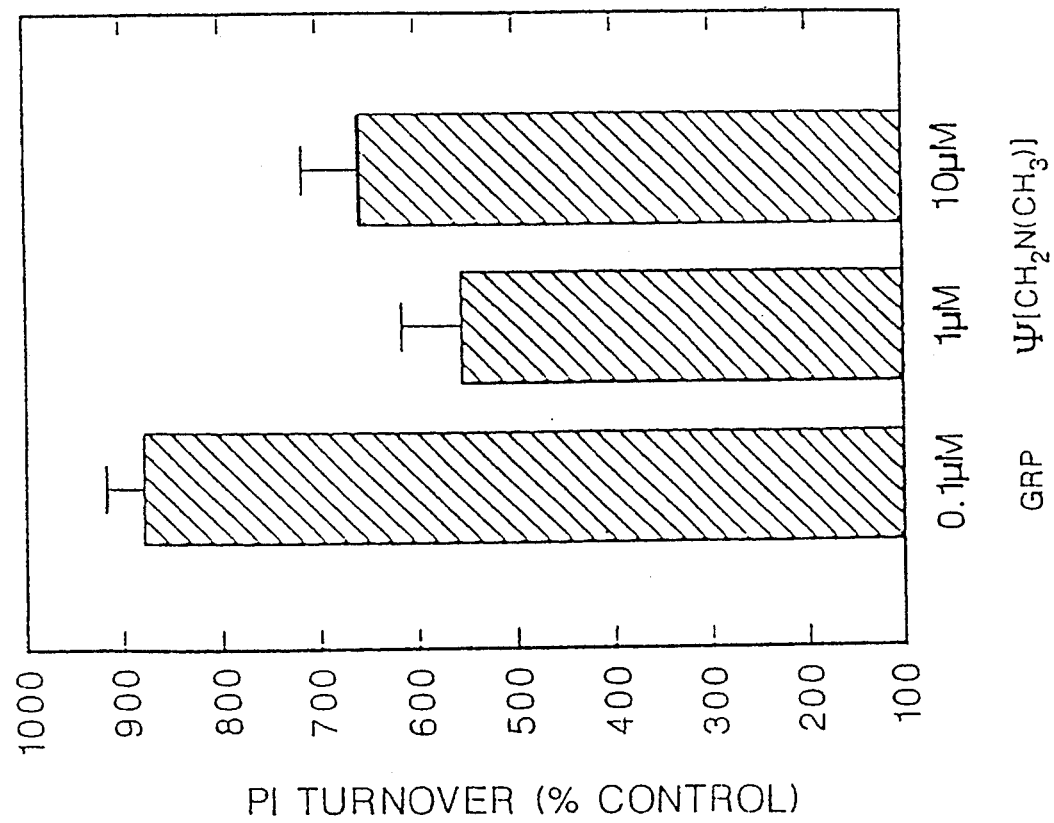
FIG. 3 illustrates the ability of GRP and litorin (NMe), to stimulate phosphatidylinositol (PI) turnover in a dose-dependent manner (Example 2).

FIG. 3 illustrates the ability of GRP and (Phe$^8$Ψ[CH$_2$N(CH$_3$)]Leu$^9$)litorin (NMe), to stimulate phosphatidylinositol (PI) turnover in a dose-dependent manner (Example 2). The ordinate (y-axis) indicates the observed PI turnover as a percentage of control. Values are mean±standard error of triplicate determinations. PI turnover by (Phe$^8$Ψ[CH$_2$N(CH$_3$)]Leu$^9$)litorin at concentrations indicated demonstrate that administration of the peptide results in a statistically significant (P<0.005) increase in PI turnover.

Table I correlates abbreviated biological and chemical nomenclature, sequences, and sequence identification numbers (ID#).

Table II compares the results of the earlier experiments (FIGS. 1-2) for receptor affinity (Kd) and PI turnover for the bombesin analogs.

TABLE 1

Sequence of Peptides and Peptide Analogs

| | | Sequence I.D.# |
|---|---|---|
| Gastrin Releasing Peptide (14-27) | Met—Tyr—Pro—Arg—Gly—Asn—His—Trp—Ala—Val—Gly—His—Leu—Met—NH$_2$ | 1 |
| Bombesin | pGlu—Gln—Arg—Leu—Gly—Asn—Gln—Trp—Ala—Val—Gly—His—Phe—Met—NH$_2$ | 2 |
| Litorin | pGlu—Gln—Trp—Ala—Val—Gly—His—Phe—Met—NH$_2$ | 3 |
| [Leu$^{13}$ψ[CH$_2$NH]Leu$^{14}$] bombesin | pGlu—Gln—Arg—Leu—Gly—Asn—Gln—Trp—Ala—Val—Gly—His—Leuψ[CH$_2$N]Leu—NH$_2$ | 4 |
| [Phe$^{13}$ψ[CH$_2$S]Leu$^{14}$] bombesin | pGlu—Gln—Arg—Leu—Gly—Asn—Gln—Trp—Ala—Val—Gly—His—Pheψ[CH$_2$S]Leu—NH$_2$ | 5 |
| [Phe$^8$ψ[CH$_2$S]Leu$^9$]litorin | pGlu—Gln—Trp—Ala—Val—Gly—His—Pheψ[CH$_2$S]Leu—NH$_2$ | 6 |
| [Phe$^8$ψ[CH$_2$S(O)]Leu$^9$] litorin | pGlu—Gln—Trp—Ala—Val—Gly—His—Pheψ[CH$_2$S(O)]Leu—NH$_2$ | 7 |
| [Phe$^8$ψ[CH$_2$N(CH$_3$)]Leu$^9$] litorin | pGlu—Gln—Trp—Ala—Val—Gly—His—Pheψ[CH$_2$N(CH$_3$)]Leu—NH$_2$ | 8 |
| [Phe$^8$ψ[CH$_2$S(CH$_3$)]Leu$^9$- litorin | pGlu—Gln—Trp—Ala—Val—Gly—His—Pheψ[CH$_2$S(CH$_3$)]Leu—NH$_2$ | 9 |
| Acetyl[D-Ala$^{11}$]bombesin (7-13)amide | Nα-acetyl-Gln—Trp—Ala—Val-D-Ala—His—Leu—NH$_2$ | 10 |
| Octyl[D-Ala$^{11}$]bombesin (7-13) amide | Nα-octyl-Gln—Trp—Ala—Val-D-Ala—His—Leu—NH$_2$ | 11 |
| Lauryl[D-Ala$^{11}$]bombesin (7-13)amide | Nα-lauryl-Gln—Trp—Ala—Val-D-Ala—His—Leu—NH$_2$ | 12 |
| Palmityl[D-Ala$^j$ bombesin (7-13)amide | Nα-palmityl-Gln—Trp—Ala—Val-D-Ala—His—Leu—NH$_2$ | 13 |

TABLE II

Comparison of affinities of bombesin and litorin analogs and their effect on PI turnover.

| Analog | Kd (nM) | Agonist$^b$ | PI Turnover % Inhibition$^c$ | Sequence I.D. # |
|---|---|---|---|---|
| Gastrin Releasing Peptide | 0.02 | + | ND | 1 |
| Bombesin | 0.15 | + | ND | 2 |
| Litorin | 0.075 | + | ND | 3 |
| [Leu$^{13}$ψ{CH$_2$NH]Leu$^{14}$]bombesin | 8.0 | — | 30* | 4 |
| [Phe$^{13}$ψ[CH$_2$S]Leu$^{14}$bombesin | 2.8 | — | 54** | 5 |
| [Phe$^8$ψ[CH$_2$S]Leu$^9$]litorin | 3.4 | — | 42* | 6 |
| [Phe$^8$ψ[CH$_2$S(O)]Leu$^9$]litorin I | 1.8 | — | 53** | 7a |
| [Phe$^8$ψ[CH$_2$S(O)]Leu$^9$]litorin II | 1.0 | — | 83** | 7b |
| [Phe$^8$ψ[CH$_2$N(CH$_3$)]Leu$^9$]litorin | .019 & 23 | + | −16 | 8 |
| Phe$^8$ψ[CH$_2$S(CH$_3$)]Leu$^9$]litorin | ND | ND | ND | 9 |
| Acetyl[D-Ala$^{11}$]bombesin(7-13)amide | 69 | — | 24 | 10 |
| Octanoyl[D-Ala$^{11}$]bombesin(7-13)amide | 5.0 | — | 82*** | 11 |
| Lauryl[D-Ala$^{11}$]bombesin(7-13)amide | 320 | — | 53** | 12 |

TABLE II-continued

Comparison of affinities of bombesin and litorin analogs and their effect on PI turnover.

| Analog | Kd (nM) | Agonist[b] | PI Turnover % Inhibition[c] | Sequence I.D. # |
|---|---|---|---|---|
| Palmityl[D-Ala11]bombesin(7–13)amide | 350 | — | 45* | 13 |

[a]The peptides listed were tested in both a competitive binding and PI-turnover assay in mouse pancreas as described in Examples 4 and 5; Kd values are averages of multiple experiments.
[b](+) represents agonist activity, (−) indicates no agonist activity, (ND) indicates not determined.
[c]For antagonist activity, % inhibition is referenced to the stimulation produced by 100 nM GRP. ND indicates not determined. Data for antagonists by the reduced bond analogs and the N-acyl analogs are from two different experiments with similar levels of GRP stimulation. *p < 0.05; p < 0.01; *p < 0.001.

What is claimed is:

1. A peptide derivative of the formula X-$A_1$-$A_2$-$A_3$-$A_4$-$A_5$-$A_6$-$A_7$-$A_8$-$\Psi$-$A_9$-Y (formula 1) wherein;

X is an amino terminal residue selected from hydrogen, one or two alkyl groups from 1 to 16 carbon atoms, one or two acyl groups of from 2 to 16 carbon atoms, carbobenzyloxy or t-butyloxy carbonyl; unless the amino terminal amino acid is a cyclic derivative and thereby X is omitted.

$A_1$ is pGlu, Glu, or a bond;
A2 is Gln;
A3 is Trp;
A4 is Ala;
A5 is Val;
A6 is Gly, Ala, or ala;
A7 is His;
A8 is Phe or Leu;

$\Psi$ is a dipeptide determinant of $A_8\Psi A_9$ wherein $\Psi$ is [$CH_2S(CH_3)$] or [$CH_2N(CH_3)$], and wherein and $A_8$ and $A_9$ designates the substituent amino acids;

A9 is Leu, Met, or Nle; and

Y is a carboxy terminal substituent of the carbonyl group of the $A_9$ amino acid selected from OH, ($C_1$-$C_8$) alkoxyester, carboxamide, mono or di ($C_1$-$C_8$) alkyl amide, ($C_1$-$C_8$) alkylamine, ($C_1$-$C_4$) thioalkylether, or pharmaceutically acceptable salt thereof.

2. Claimed is a peptide of claim 1 wherein the peptide is Gln—Trp—Ala—Val—Gly—His—Phe$\Psi$[$CH_2N(CH_3)$]Leu—$NH_2$.

3. A peptide of one of claims 1 or 2 which may be a pharmaceutically acceptable salt thereof or a pharmaceutical composition which utilizes a pharmaceutically acceptable carrier.

4. A method of stimulating digestion in a patient in need thereof, which comprises administering to the patient a therapeutic amount of a peptide of one of claims 1 or 2.

5. A method of decreasing food intake in a patient in need thereof which comprises administering to the patient a therapeutic amount of a peptide derivative of one of claims 1 or 2.

6. A method of stimulating growth of organ tissues, wherein tissues of lung, pancreatic, or intestinal origin, in a patient in need thereof which comprises administering to the patient a therapeutic amount of a peptide derivative of one of claims 1 or 2.

7. A method of temporarily stimulating growth of a tumor to increase susceptibility to chemotherapeutic agents which comprises administering to a patient in need thereof a therapeutic amount of a peptide derivative of one of claims 1 or 2.

8. A method of stimulating natural killer cell activity against tumor cells by administering to a patient in need thereof a therapeutic amount of a peptide derivative of one of claims 1 or 2.

9. A process for preparing a peptide derivative according claims 1 or 2 or a pharmaceutically acceptable salt thereof comprising the steps of:
 a) using a resin with a suitably bound C-terminal protected dipeptide from the group $A_8\Psi A_9$, wherein $\Psi$ is $[CH_2S(CH_3)]$ or $[CH_2N(CH_3)]$ and $A_8$ and $A_9$ designates the substituent amino acids;
 b) sequentially coupling the other alpha amino protected amino acids, $A_7$ through $A_1$ to achieve the protected amino acid sequence claimed; optionally having amino acid extension of the group C and N; and optionally having modification selected from species X and Y.
 c) removing said protecting groups;
 d) purifying the desired peptide.

* * * * *

UNITED STATES PATENT AND TRADEMARK OFFICE
CERTIFICATE OF CORRECTION

Page 1 of 3

PATENT NO. : 5,428,019
DATED : June 27, 1995
INVENTOR(S) : Judson V. Edwards, et. al.

It is certified that error appears in the above-indentified patent and that said Letters Patent is hereby corrected as shown below:

Column 2, line 15, the patent reads "TEE", and should read --THE --.

Column 2, line 30, the patent reads "a natural variants", and should read --a natural variant --.

Column 3, line 46, the patent reads "arian", and should read --avian --.

Column 4, line 43, the patent reads "a internally", and should read --an internally --.

Column 4, line 52, the patent reads "either the of the", and should read --either of the --. a Column 5, line 9, the patent reads "made up three", and should read --made up of three --.

Column 8, line 22, the patent reads "with with", and should read --with --.

Column 8, line 32, the patent reads "can done", and should read --can be done --.

Column 8, line 38, the patent reads "linkagae", and should read --linkage --.

Column 9, line 31, the patent reads "of of", and should read --of --.

Column 9, line 34, the patent reads "aidehyde", and should read --aldehyde --.

Column 10, line 31, the patent reads "stir for from", and should read --stir from --.

Column 10, line 35, the patent reads "stir for from", and should read --stir from --.

UNITED STATES PATENT AND TRADEMARK OFFICE
CERTIFICATE OF CORRECTION

PATENT NO. : 5,428,019
DATED : June 27, 1995
INVENTOR(S) : Judson V. Edwards, et. al.

It is certified that error appears in the above-indentified patent and that said Letters Patent is hereby corrected as shown below:

Column 9, Method A beginning on line 44-62, the patent reads "

1) 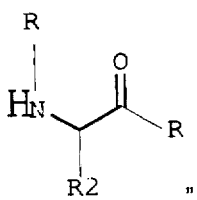  1) 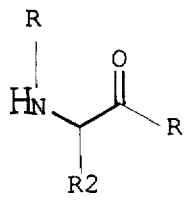

", and should read -- -- .

Column 11, line 8, the patent reads "    resents ", and should read -- ® represents --.

Column 11, line 20, the patent reads "wherein     represents", and should read --wherein ® represents --.

Column 11, line 21, the patent reads "a amino", and should read --an amino --.

Column 11, line 31, the patent reads "reaction with with", and should read --reaction with --.

Column 12, line 4, the patent reads "G-amino", and should read --α-amino --.

Column 12, line 32, the patent reads "a either a", and should read --either an --.

Column 14, line 64, the patent reads "these effect", and should read --these effects --.

Column 15, lines 63-64, the patent reads "soft tissue Barcomas, osseus, or non-osseous Barcomas,", and should read -- soft tissue sarcomas, osseus, or non-osseous sarcomas --.

UNITED STATES PATENT AND TRADEMARK OFFICE
CERTIFICATE OF CORRECTION

PATENT NO. : 5,428,019
DATED : June 27, 1995
INVENTOR(S) : Judson V. Edwards, et. al.

It is certified that error appears in the above-indentified patent and that said Letters Patent is hereby corrected as shown below:

Column 16, line 56, the patent reads "whereby the the" and should read --whereby the --.

Column 16, line 64, the patent reads "requires such need" and should read --requires such needed Column 17, line 41, the patent reads "exacted" and should read --extracted --.

Column 19, line 11, the patent reads "dicloromethane" and should read --dichloromethane --.

Column 21, line 29 - Sequence ID #3, the patent reads "pGlu-Gin", and should read --pGlu-Gln --.

Column 21, line 46 - Sequence ID #13, the patent reads "Palmityl[D-Ala] bombesin", and should read -- Palmityl[D-Ala$^{11}$] bombesin --.

Column 36, line 3, the patent reads "according claims 1 or 2", and should read -- according to claims 1 or 2--.
On the cover page of the patent, item 57 ABSTRACT, the patent reads "Agonists and Antagonist of bombesin are derivatives of", and should read --Disclosed are Agonists and Antagonist of bombesin which are derivatives--.

Signed and Sealed this

Eighteenth Day of November 1997

Attest:

BRUCE LEHMAN

*Attesting Officer*    *Commissioner of Patents and Trademarks*